(12) United States Patent
Prasad et al.

(10) Patent No.: US 8,004,676 B1
(45) Date of Patent: Aug. 23, 2011

(54) METHOD FOR DETECTING ANALYTES USING SURFACE PLASMON RESONANCE

(75) Inventors: Paras N. Prasad, Williamsville, NY (US); Przemyslaw P. Markowicz, Woodbury, MN (US); Wing Cheung Law, Amherst, NY (US); Andrei Kabashin, St.-Leonard (CA); Sergiy Patskovsky, Montreal (CA)

(73) Assignee: The Research Foundation of State University of New York, Amherst, NY (US)

( * ) Notice: Subject to any disclaimer, the term of this patent is extended or adjusted under 35 U.S.C. 154(b) by 650 days.

(21) Appl. No.: 12/069,700

(22) Filed: Feb. 11, 2008

Related U.S. Application Data

(60) Provisional application No. 60/889,036, filed on Feb. 9, 2007.

(51) Int. Cl.
*G01J 4/00* (2006.01)
(52) U.S. Cl. ......................................... 356/369
(58) Field of Classification Search .................. 356/364, 356/369
See application file for complete search history.

(56) References Cited

U.S. PATENT DOCUMENTS

| | | | | |
|---|---|---|---|---|
| 5,229,833 A | * | 7/1993 | Stewart | 356/364 |
| 5,468,606 A | * | 11/1995 | Bogart et al. | 435/5 |
| 5,494,829 A | * | 2/1996 | Sandstrom et al. | 436/518 |
| 5,631,171 A | * | 5/1997 | Sandstrom et al. | 436/518 |
| 6,573,107 B1 | | 6/2003 | Bowen et al. | |
| 6,594,011 B1 | * | 7/2003 | Kempen | 356/369 |
| 6,937,341 B1 | * | 8/2005 | Woollam et al. | 356/436 |
| 6,970,249 B1 | | 11/2005 | Lipson et al. | |
| 7,002,686 B2 | * | 2/2006 | Lieberman et al. | 356/369 |
| 7,023,547 B2 | * | 4/2006 | Venkatasubbarao et al. | 356/369 |
| 7,193,711 B2 | * | 3/2007 | Rassman et al. | 356/369 |
| 7,283,234 B1 | * | 10/2007 | Woollam et al. | 356/369 |
| 7,286,221 B2 | * | 10/2007 | Caracci et al. | 356/300 |
| 7,586,607 B2 | * | 9/2009 | Sun | 356/364 |
| 2002/0093654 A1 | * | 7/2002 | Lieberman et al. | 356/369 |
| 2003/0030817 A1 | | 2/2003 | Lee et al. | |

(Continued)

FOREIGN PATENT DOCUMENTS

DE   10 2004 027 957 A1   12/2005

(Continued)

OTHER PUBLICATIONS

Law, et al.; Wide dynamic range phase-sensitive surface Plasmon resonance biosensor based on measuring the modulation harmonics; Biosensors and Bioelectronics, 2007, vol. 23; pp. 627-632.

(Continued)

*Primary Examiner* — Patrick J Connolly
(74) *Attorney, Agent, or Firm* — Hodgson Russ LLP

(57) ABSTRACT

A method is provided for detection of analytes using the Surface Plasmon Resonance effect. The method comprises providing a metal film on a transparent substrate. The free surface of the metal film is exposed to a test sample. An anlyte in the sample can interact directly with the metal film or via analyte binding molecules (ABMs) complexed to the film. Light is directed incident to the surface of film in contact with the substrate. Light is reflected from the surface of the film under SPR conditions. The reflected light is collected and the second and/or third harmonics of the resulting electrical signal, which are indicative of the phase and polarization state of the reflected light, are determined. The second and third harmonics are correlated to the presence and/or concentration of the analyte.

20 Claims, 6 Drawing Sheets

U.S. PATENT DOCUMENTS

| | | | |
|---|---|---|---|
| 2003/0219809 A1 | 11/2003 | Chen et al. | |
| 2004/0207846 A1* | 10/2004 | Rassman et al. | 356/369 |
| 2005/0105091 A1* | 5/2005 | Lieberman et al. | 356/369 |
| 2005/0186565 A1 | 8/2005 | Malak | |
| 2006/0119859 A1 | 6/2006 | Su et al. | |
| 2010/0238443 A1* | 9/2010 | Claypool et al. | 356/369 |
| 2010/0259754 A1* | 10/2010 | Hooper et al. | 356/369 |

FOREIGN PATENT DOCUMENTS

| | | |
|---|---|---|
| JP | 2003-344273 | 12/2003 |
| JP | 2005-156414 | 6/2005 |

OTHER PUBLICATIONS

Markowicz, et al.; Phase-sensitive time-modulated surface Plasmon resonance polarimetry for wide dynamic range biosensing; Optics Express, Feb. 19, 2007, vol. 15, No. 4; pp. 1745-1754.

Homola, et al.; Surface Plasmon resonance sensors: review; Sensors and Actuators B, 1999, vol. 54; pp. 3-15.

* cited by examiner

METHOD FOR DETECTING ANALYTES USING SURFACE PLASMON RESONANCE

This application claims priority to U.S. provisional application No. 60/889,036 filed Feb. 9, 2007, the disclosure of which is incorporated herein by reference.

This work was supported by funding from the Government under grant no. FA9550-04-1-0158 from the United States Air Force/Air Force Office of Scientific Research. The Government has certain rights in the invention.

BACKGROUND OF THE INVENTION

Surface Plasmon Resonance (SPR) occurs when surface plasmon waves, which are collective oscillations of electrons in a metal, are excited at a metal/dielectric interface. Light is directed at, and reflected from, the side of the metal film surface not in contact with the sample. SPR causes a reduction in the reflected light intensity at a specific combination of angle and wavelength. Biomolecular binding events lead to a change in the refractive index and thickness of an ultra-thin organic (dielectric) layer on the metal film, which changes the SPR resonance conditions resulting in an extremely high sensitivity response. SPR methodology does not require a time-consuming labeling step, and reaction kinetics constant can be routinely obtained within minutes.

Commercially available SPR-based devices use light intensity (angular or spectral position of SPR minimum) as the information source. The detection limit of conventional SPR devices is of the order of $10^{-5}$ or higher in terms of refractive index change ($5\times10^{-6}$ in advanced configurations with acoustic-optical modulators). This corresponds to a minimum detection limit of about 1 pg per $mm^{-2}$ of biomaterial accumulating at the biosensor surface. In general, this sensitivity is sufficient to study molecular interactions, for example antibody-antigen, protein-DNA, DNA-DNA, receptor-ligand, etc.

The SPR interferometry approach, in which information on phase is extracted optically from spatial interference pattern formed by interfering signal and reference (non-affected by SPR) beams, is a common approach. This approach gives high sensitivity and possibility of lateral resolution, but has disadvantages such as narrow dynamic range, low noise immunity, and a complicated image treatment. Alternatively, using an polarimetric approach, information on phase can be obtained from the analysis of the ellipse of polarization. In particular, a polarimetric scheme, in which phase information was studied with the help of a rotating analyzer and electro-optic modulators, has been reported. Such approach improved noise immunity and enabled to apply electronic processing for signal filtering. However, the dynamic range of measurements remained narrow, and the measurement procedure was complicated.

Based on the foregoing, there is an ongoing need to develop SPR methodology with high sensitivity and wide dynamic range. SPR methodology with these qualities would be very useful in the analysis of biological and chemical samples, particularly in the detection of small molecular weight analytes (such as molecules with a mass of less than 1000 Daltons) and other biomolecules.

SUMMARY OF THE INVENTION

The present invention provides a sensitive method for the detection of analytes. In the method of the present invention, a transparent substrate, which has a metal film thereupon, is used. The metal film is of a thickness such that it is capable of exhibiting surface plasmon resonance. On the free surface of the metal film are complexed analyte binding molecules (ABMs) so that the analyte binding domain of the ABMs is available for analyte binding. The ABM complexed side of the metal film is contacted with a test solution and incident light is directed at the other surface of the film (i.e., the surface which is in contact with the substrate). The reflected light from the metal film is converted to an electrical signal, the electrical signal being representative of the polarization and phase of the reflected light, and the second and third harmonics are determined and compared to predetermined controls to identify the presence or absence of an analyte in the test sample.

In one embodiment, the analyte may be detected directly via interaction with the metal film surface without the need for ABMs.

DESCRIPTION OF THE INVENTION

Figure 1:
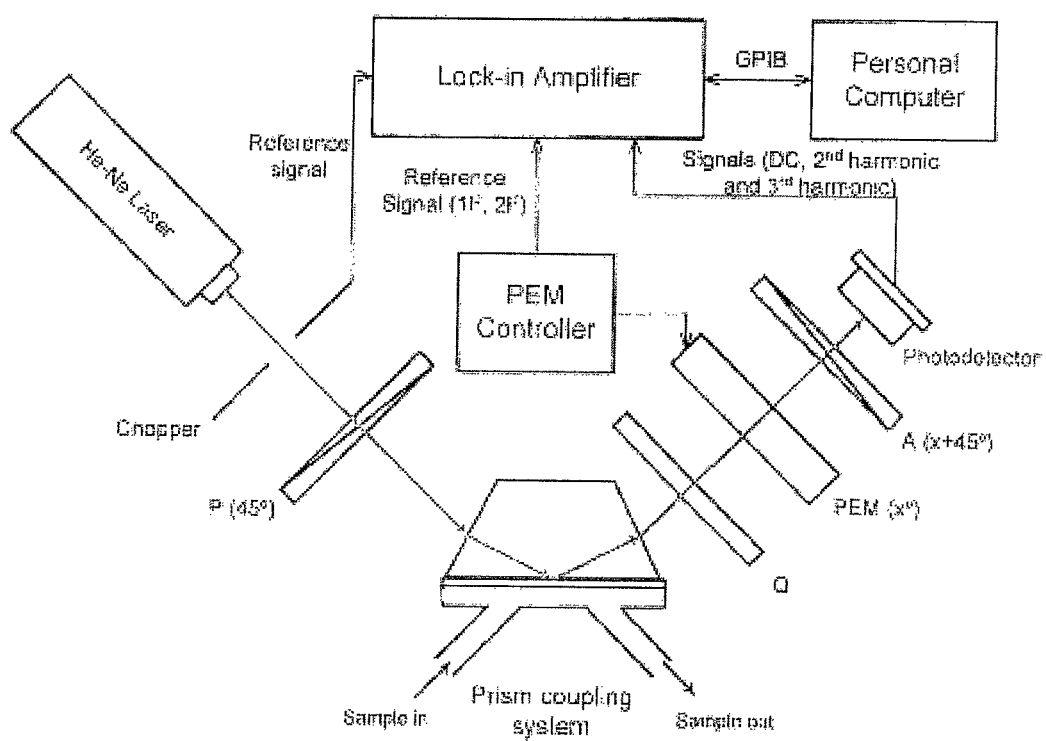
FIG. 1. Schematic configuration of one embodiment of a SPR optical sensor. P, polarizer; Q, adjustable retarder; PEM, photoelastic modulator; A, analyzer.

The present invention describes a polarimetry-based surface plasmon resonance (SPR) methodology that exhibits high phase sensitivity and wide dynamic range using a simple instrumental arrangement. The scheme involves simple optical elements and a photoelastic modulator to simultaneously extract phase and polarization characteristics of light reflected under SPR conditions in two different channels.

The method for detection of an analyte using the present invention comprises the following steps: providing a transparent substrate having a metal film thereupon, said metal film capable of exhibiting surface plasmon resonance and having analyte binding molecules (ABMs) complexed thereto such that the analyte binding domain of the ABMs is available for analyte binding; contacting the surface of the metal film on which the ABMs are complexed with a test sample so that the analyte binding domains of the ABMs are exposed to the test sample; directing incident light on the surface of the metal film in contact with the substrate to generate reflected light; converting reflected light to an electrical signal, wherein the electrical signal is representative of the polarization and phase of the reflected light; and determining second and third harmonics of the electrical signal, wherein a difference between the second and/or third harmonics obtained from the test sample and a predetermined control is indicative of the presence or absence of the analyte in the test sample.

The advantages of this invention include: high detection sensitivity; wide dynamic range of measurements; simple instrumental design; simultaneous extraction of both light polarization and phase changes; and the potential for multiple-sensing. The detection limit for refractive index change, obtained in our experiments, was at least $1.7 \times 10^{-6}$, which is almost one order of magnitude lower than in conventional SPR systems. The detection limit in our experiments was limited by temperature drifts rather than by instrumental noises. In one embodiment, to further improve the detection limit, thermostats or differential schemes can be used. Monitoring the $2^{nd}$ and $3^{rd}$ harmonics can combine highly sensitive phase sensitivity with wide dynamic range of polarization sensitivity. This is an improvement over other polarimetry or interferometry schemes that are not able to provide such a wide dynamic range. Unlike the present method, alignment is critical in the SPR interferometry method and the method is sensitive to any vibration. In one embodiment, our system uses a single beam, single detector approach. However, in another embodiment multiple-analyte monitoring is possible by scanning the laser beam across the sample (for example using galvano-mirrors) and detecting the signal from each sample point separately. Such a device can simultaneously monitor multiple of biomolecular interactions in a single run experiment.

The present invention is useful for detection of any type of analyte which interacts directly with the metal surface or with a binding partner complexed to the metal film. Applications for this invention include, but are not limited to, drug discovery (real-time, label-free detection of low molecular weight drugs); proteomics (studies of reactions involving small molecular weight proteins); rapid detection and analysis of small concentration of deadly viruses and bacteria; and environmental monitoring.

Figure 2:
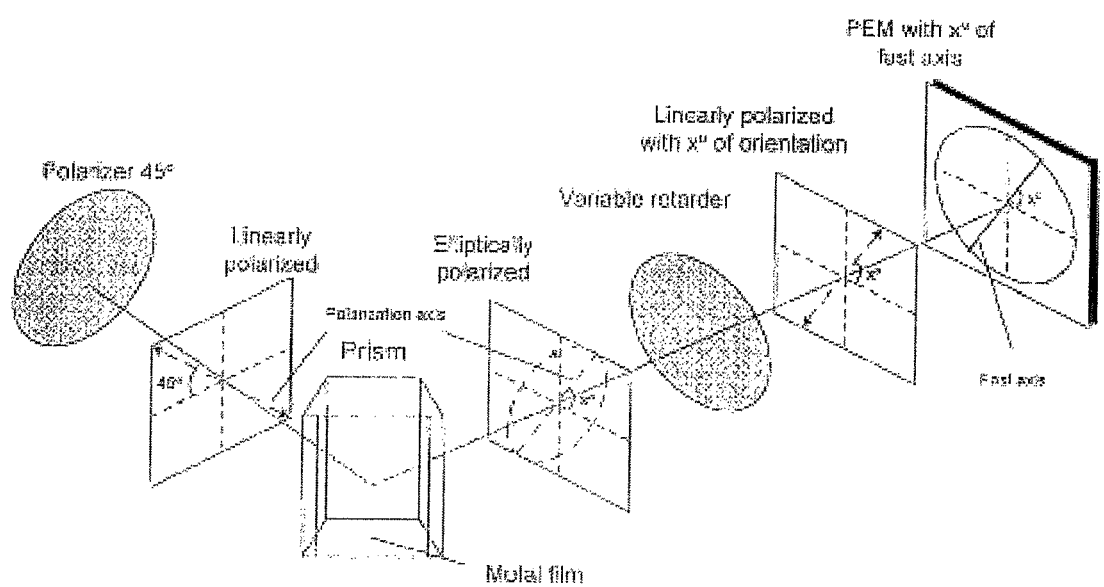
FIG. 2. Graphical representation of polarization geometry of the beam after passing through the SPR sensor head. Both the orientation and retardation have changed.

The present invention introduces a new way of detecting phase and polarization changes in SPR based sensors. The method employs periodic modulation of the illuminating light for the simultaneous detection of the light phase and polarization. The method uses s-polarized light, not affected by SPR, as a reference beam, while information on the phase of the p-polarized component is obtained from an analysis of phase-polarization state of light of mixed polarization. A schematic diagram of an example of an instrumental configuration useful in practicing the method of the present invention is shown in FIG. 1. In one embodiment, the experimental set-up comprises a light source; a polarizer; a metal layer on a transparent substrate; a phase retarder; a photoelastic modulator (PEM); a polarizer; and a detector. While an illustrative order of the components is shown, it will be recognized that this order can be changed. In one embodiment, the light is passed sequentially through a phase retarder, a photoelastic modulator, a polarizer, and a photodetector, and processing the electrical signal from the photodetector using a lock-in amplifier. FIG. 2 is a representation of the polarization state of the light that travels through the various components.

The light source supplies the incident light, wherein the incident light is coherent light. The incident light can be from 630 nm to 1050 nm. In one embodiment, the wavelength is 785 nm. Examples of light sources useful in the present method: a 50 mW He—Ne laser operating at a wavelength of 633 nm; and a 40 mW laser (such as the laser available from CUBE, Coherent) operating at a wavelength of 785 nm. A chopper is used to minimize noise related to drifts in laser intensity. A pi/4 waveplate can be used to generate a 45 degree linearly polarized beam without affecting the intensity of the beam.

The polarization state of the incident light beam is established using, for example, a polarizer. Examples of polarizers useful in the present invention include, but are not limited to, those available from Edmund Optics (TECHSPEC NIR Linear Polarizer, wavelength range 750-850 nm) and OptoSigma (Dichroic Polarizer, wavelength range 400-750 nm)

The incident light is directed through a transparent substrate, such as a prism, and on to the side of the metal layer in contact with the transparent substrate and not in contact with the test sample to excite SPR. The transparent substrate serves to couple the incident light to the metal layer such that SPR can be excited. The transparent substrate should have a refractive index greater than that of the dielectric layer formed by the interaction of the analyte with the metal surface either directly or through the ABMs. For example, incident light is directed on to a prism coupling system, such as depicted in FIG. 1. Examples of other coupling systems useful for exciting SPR are gratings, and optical fibers. Examples of prism materials useful in the present method are glass (such as BK7 or SF11 glass), quartz, and plastic. Examples of prisms useful in the present method are a F2 equilateral prism (Melles Griot), and a hemispherical prism.

The transparent substrate is at least partially covered by a metal layer (also referred to herein as a film). For example, the base of a prism is at least partially covered by a metal layer. Examples of metals useful in the present method are gold and silver. In one embodiment, there can be more than one layer on the substrate. The multiple layers may be of the same or different metal. The metal films should be high purity. For example, metals with purity levels of at least 95% are useful in the present invention. In various embodiments, the metal films can be of 96, 97, 98 or 99% purity. In a preferred embodiment, metals with a purity of at least 99.99% are used. The thickness of the film layer is such that surface plasmon resonance is exhibited. A thickness of from 45 to 55 nm is suitable to achieve SPR. In various embodiments the thickness of the film is 45, 46, 47, 48, 49, 50, 51, 52, 53, 54 and 55 nm. In a specific embodiment, the thickness of the metal film is 50 nm. The metal film can be, for example, deposited by a thermal or electron-beam evaporator on the surface of the prism or on a glass plate or slide. In one embodiment, the transparent substrate is at least partially covered by a plurality of metal layers. For example, the metal layer can comprise a silver layer at least partially covering the transparent substrate and a gold layer on top of the silver layer and vice versa.

In another embodiment the transparent substrate comprises a glass slide or plate in immersion contact with the prism using a refractive index matching medium (such as Santovac SL-5262 oil) dispersed between the glass slide and prism. A glass plate coated with a thin metal film (such as a 50 nm gold film, commercially available from Platyus Technologies) is useful in the present invention. The angle of light incident on the metal film is selected so as to produce SPR coupling and excite surface plasmons over the metal layer/dielectric medium (layer) interface. The SPR effect results in a significant decrease of intensity of p-polarized component and a sharp change of its phase, changing the total polarization state.

The metal film is exposed to a test sample in which the presence or absence of the abalyte is to be detected. An analyte is any compound, molecule, biomolecule, etc. which can interact with the metal film, either directly or via ABMs complexed to the metal film, such that its presence and/or concentration can be determined as a result of a change in the SPR effect. The analyte can be in the form of a liquid, or a gas, or in solution, or combinations thereof. Examples of analytes include, but are not limited to, large molecules such as proteins (53 kDa-3000 kDa), antibodies (~150 kDa), and biotin (or vitamin B7), and small molecules such as hapten, DNA, and hormones (e.g. insulin (~6 kDa)).

The test sample can interact with the metal layer in a variety of ways. For example, the analyte can be introduced as a solution, and the solution can be essentially stationary over the metal layer or the solution may flow over the metal layer. A peristaltic pump can be used to flow a test sample solution over the metal layer. In another example, useful for biomolecule sensing, an analyte binding molecule (ABM), examples of which include receptors, proteins, enzymes, antibodies, DNA conjugates, any molecule with a specific affinity for another molecule, or analyte binding fragments thereof, is immoblized on the metal layer surface. The ABM is immobilized on the metal surface such that the analyte binding domain of the ABM, e.g. the epitope of an antibody, is available for binding an analyte. The ABM can be immobilized directly on the metal layer surface. Preferably, the metal surface is functionalized, with a self-assembled monolayer of thiols for example, and ABMs are introduced as tail groups on the functionalizing agent, the thiol in the example. Another example of a functionalization of the metal layer surface is to react the self-assembled monolayer with dextran using epichlorohydrin. Treatment of the covalently bound dextran molecules with iodoacetic acid results in formation of carboxylic acid groups which can be used immoblize ABMs in a variety of ways. For a review of functionalization see Mullett, et al. "Surface Plasmon Resonance-Based Immunoassays" METHODS 22, 77-91 (2000).

The incident light is reflected from the side of the metal layer in contact with the transparent substrate and not in contact with the test sample. A phase (or variable) retarder is used to compensate the ellipticity (phase shift between the s- and p-component) of light reflected from the metal film which is caused by SPR. In one instrumental configuration a quarter wave plate with its axis parallel the optical path of the system can be used as the phase retarder. When water is in contact with gold, the phase shift between s- and p-component is about 90 degrees. Therefore the beam becomes near-linearly polarized with x degree orientation of polarization after passing through the quarter wave plate. Alternatively, a Bobinet-Soleil or other highly accurate phase compensator is used as the variable retarder resulting in better compensation of the phase difference of the reflected light.

In a preferred embodiment the method comprises a variable retarder, wherein the variable retarder compensates the change in phase of the reflected light resulting from the surface plasmon resonance effect due to the test sample minus the analyte, i.e. the variable retarder sets a phase condition or baseline. For example, where a test sample comprises an analyte contained in a solution (e.g. a protein in a buffer solution) the variable retarder is used to set the initial phase condition using a test sample without the protein. The variable retarder plays an important role in the response of the second and the third harmonic signals to the polarization and the phase change caused by SPR. It is important that the relative contributions of signals from the second and third harmonics depend on whether the phase shift due to SPR is precompensated by the phase retarder or not, giving rise to different regimes of system operation. Without compensating the phase introduced by SPR, the second harmonic signal exhibits a shorter dynamic range than the third harmonic signal. The second harmonic and third harmonic are affected by two different properties of the optical beam, the former predominantly by the polarization amplitude and the latter by the phase. By utilizing these two characteristics simultaneously, one can detect a small change of refractive index, which is indicative of a corresponding change in the analyte concentration or level of biomolecular interaction, over a wide dynamic range.

A photoelastic modulator (PEM) is used to sensitively control variations of phase of p-component. Initially, the phase compensated beam is passed through the PEM which is oriented in such a way that the PEM does not modulate the beam. However, the modulation starts to occur when phase of p-component changes due to a variation of refractive index of the adjacent medium and the beam becomes elliptical. The PEM is used to sinusoidally modulate the p-component at a fixed frequency, e.g. 42 kHz. PEM polarimetry has the advantage that the signal is modulated at a high frequency (and often detected with a lock-in amplifier), excluding many sources of noise not at the PEM operating frequency and attenuating the white noise by the bandwidth of the lock-in amplifier. An example of a PEM that is useful in the present method is a Hinds PEM-90.

The polarizer converts the polarization state of the reflected light to an intensity. In one embodiment, a polarizer (analyzer) is placed downstream of the PEM and oriented x+45 degrees in front of the detector.

The photodetector converts the reflected light, an optical signal, to an electrical signal. In one embodiment, a photodetector is placed downstream of the polarizer. An example of a photodetector is a silicon detector. In one embodiment the silicon detector has a higher frequency response than the fixed frequency of the PEM. Information on the phase-polarization state of light reflected under SPR is extracted from 2nd and 3rd harmonics of modulated signal from the photodetector using a lock-in amplifier. Examples of lock-in amplifiers useful in the present invention include, but are not limited to, those available from Signal Recovery (e.g. Model7280 (Dual channel), and Model7265 (Single channel). In one embodiment DC, 2nd harmonic and 3rd harmonic signals are detected simultaneously requiring 3 channels. The use of the $2^{nd}$ and $3^{rd}$ harmonics and lock-in amplifier is preferable because it is easier to filter external noise. In one instrumental configuration, the second and third harmonic signals are monitored in real-time using a computer program (such as a LabView program) run on a personal computer that is connected to the lock-in amplifier.

In practice, a solution or sample without the analyte or with a known concentration of the analyte is used to determine a baseline (or 1 or more predetermined control values or states) for the SPR effect. The test sample is introduced on the metal layer and a change in the SPR effect, relative the baseline or predetermined control, determined. The change in the SPR effect is measured by determining the change in the second and/or third harmonics of the electrical signal generated by the photodetector resulting from the reflected light impinging on the detector. While not intending to be bound by any particular theory, it is considered that the change in the second and/or third harmonics is based on a change of the refractive index and thickness of the dielectric layer at the metal surface resulting from interaction of the analyte with metal surface or interaction of the analyte with an ABM immobilized on the metal film. This change in the second and/or third harmonics can be correlated with the presence and concentration of the analyte in the test sample.

The dynamic range of the current method is used for SPR phase measurement at a fixed incident angle. The present invention may be very useful in arrayed biosensing applications using where the optical design does not permit measurements at multiple angles, i.e. the technique itself can reduce two-dimensional optical detector arrays to one-dimensional ones by requiring a linear array of optical detectors for locating the SPR dip for each biosensor site.

The following examples are included to illustrate the invention and are not intended to be restrictive:

EXAMPLE 1

This example describes detecting the presence of and measuring the concentration of the glycerine. This example also demonstrates the high sensitivity of the present polarimetry-based SPR system. The response of $2^{nd}$ and $3^{rd}$ harmonics was examined when liquids with different refractive indices were brought into contact with the gold layer. For these tests, standard CM5 chips (thin gold film (approximately 50 nm) on a glass slide; Biacore) were used. In this chip, the thickness of the gold film is well optimized to provide a sharp jump of phase of light reflected under SPR.

Figure 3:
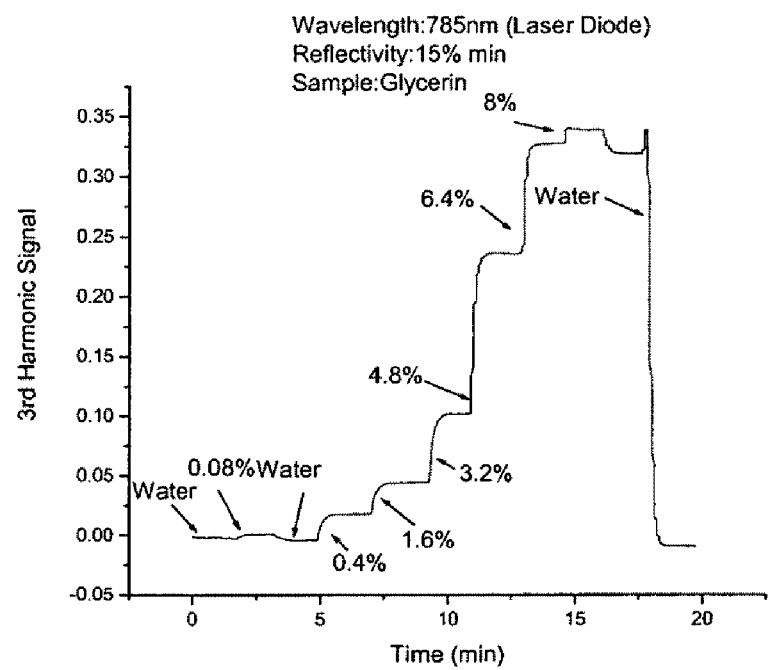
FIG. 3. Graphical representation of responses of the $3^{rd}$ and $2^{nd}$ harmonics to the variation of the concentration of glycerin in water.
Figure 3:
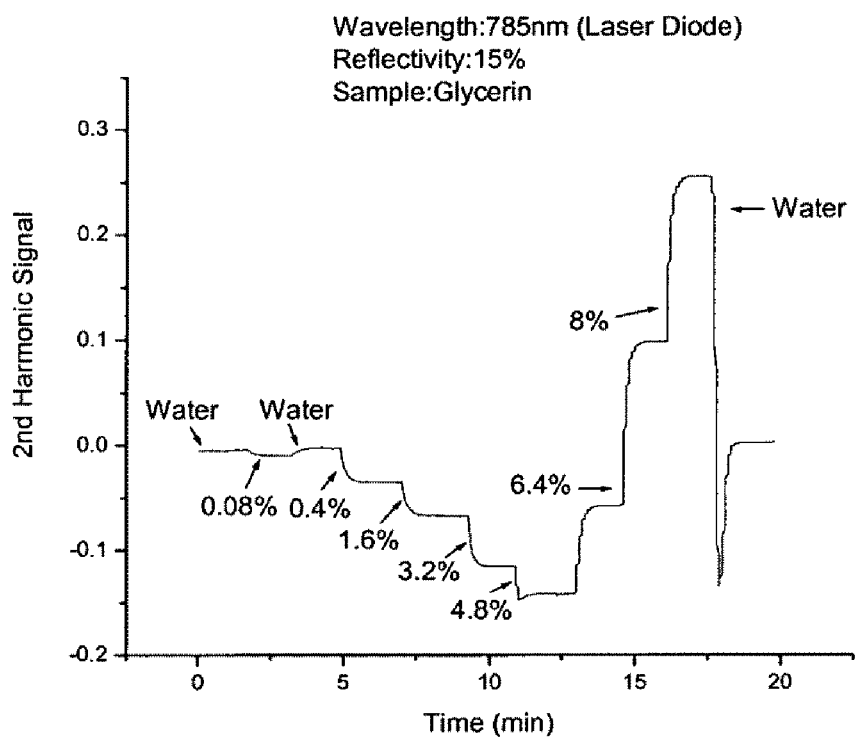
Figure 4:
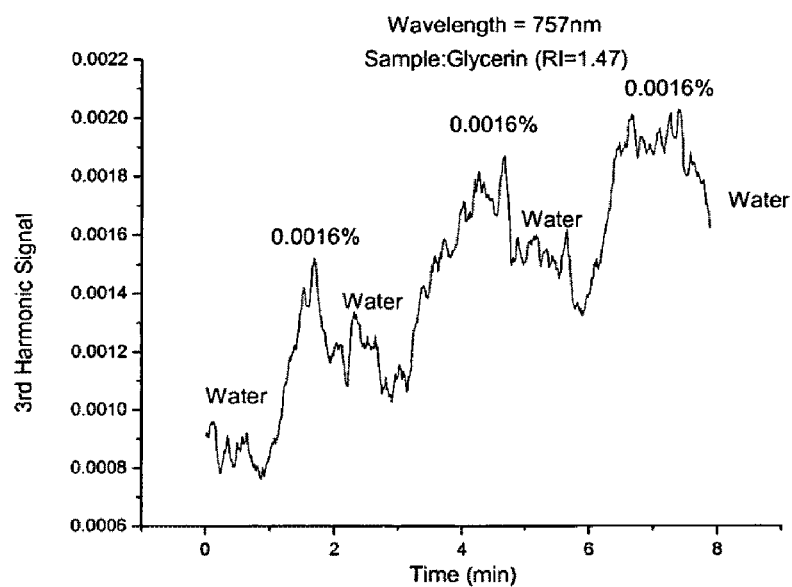
FIG. 4. Graphical representation of response of the $3^{rd}$ harmonic as a function of the refractive index change.
Figure 5:
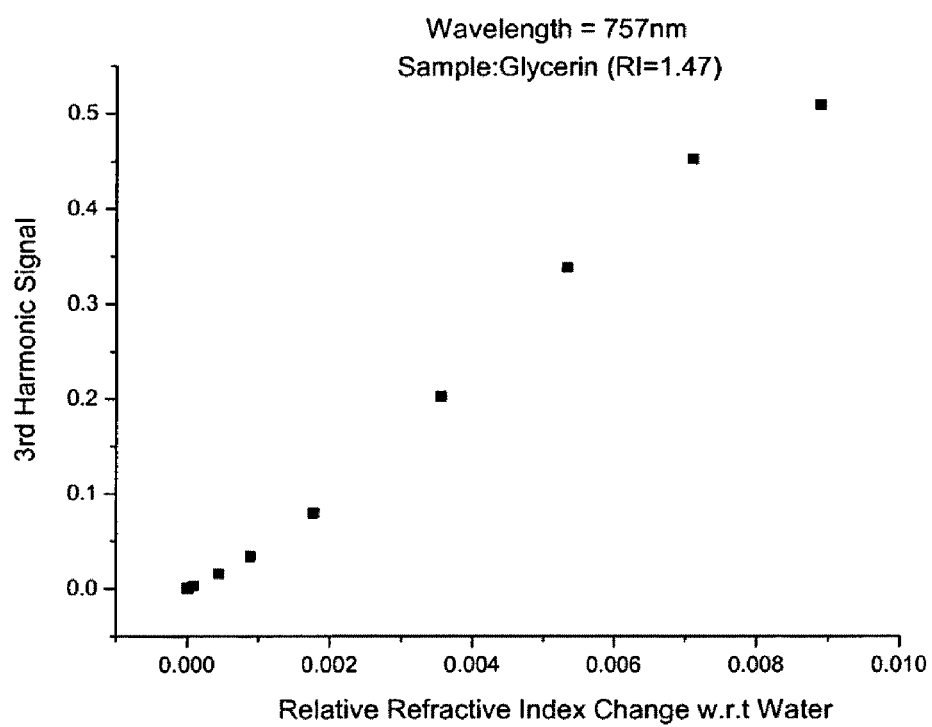
FIG. 5. Graphical representation of relationship between $3^{rd}$ harmonic signal and relative refractive index change.

Using a peristatic pump, solutions of water with different concentrations of glycerine were introduced onto the metal layer. Knowing the difference between refractive indices of glycerine and water, calibration and determination of the detection limit of our system was achieved. FIG. 3 shows typical responses of $2^{nd}$ and $3^{rd}$ harmonics, corresponding to polarization- and phase sensitivities, respectively, to different concentrations of glycerin. One can see that both channels, $2^{nd}$ and $3^{rd}$ harmonics, could follow relatively strong changes of glycerin concentration. Nevertheless, we found that the $3^{rd}$ harmonics has better sensitivity than the $2^{nd}$ one. In particular, $3^{rd}$ harmonic could follow a small change of glycerin concentration, corresponding to the change of refractive index of $1.7 \times 10^{-6}$ (FIG. 5), whereas the $2^{nd}$ harmonic required 5-times higher concentration to provide a detectable response.

EXAMPLE 2

This example describes detecting the presence of and measuring the concentration of the dimethyl sulfoxide (DMSO). This example further demonstrates the high sensitivity and broad dynamic range of the present polarimetry-based SPR methodology. Different concentrations of DMSO/water solutions were used in our experiment. The corresponding refractive index change relative to pure water (0%) is listed in Table 1.

TABLE 1

| Weight ratio (%) | Change in Refractive Index |
|---|---|
| 0.01 | $1.33 \times 10^{-5}$ |
| 0.05 | $6.64 \times 10^{-5}$ |
| 0.1 | $1.33 \times 10^{-4}$ |
| 0.05 | $6.64 \times 10^{-4}$ |
| 1 | $1.33 \times 10^{-3}$ |
| 2 | $2.66 \times 10^{-3}$ |
| 4 | $5.31 \times 10^{-3}$ |
| 8 | $1.06 \times 10^{-2}$ |

Figure 6:
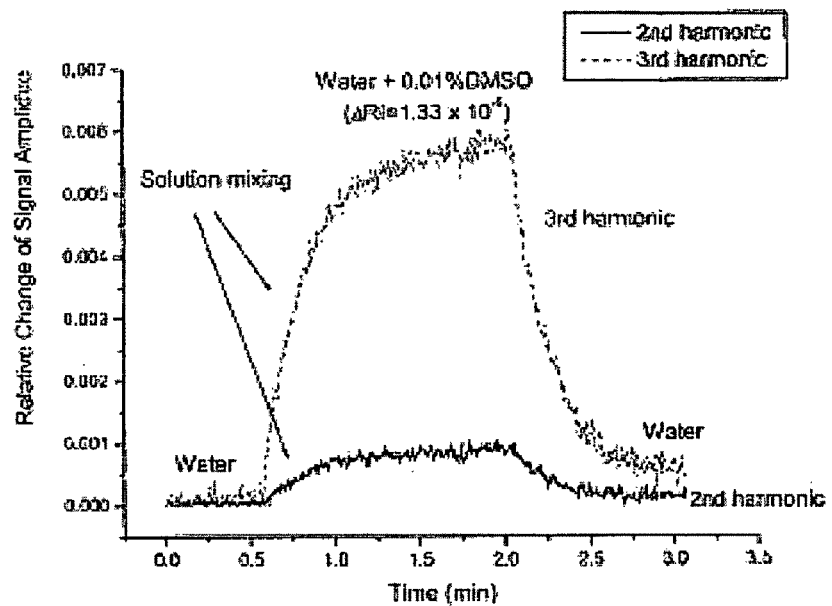
FIG. 6. Graphical representation of response of the $2^{nd}$ and $3^{rd}$ harmonics as a function of the refractive index change.

Two solutions, water and water with 0.01% of DMSO whose refractive index difference is $1.33 \times 10^{-5}$, were introduced sequentially to the sensor head using a peristaltic pump. FIG. 6 shows a typical response curves. From the graphs, we can see that 0.00582 units (3rd harmonic) and 0.000952 units ($2^{nd}$ harmonic) have been changed after adding 0.01% of DMSO to the sensor head. This demonstrates that 3rd harmonic gives us higher detection sensitivity. The amplitude fluctuation obtained in FIG. 6 is about 0.000413 units. Based on that stability, we estimate the detection limit of our system is $9.44 \times 10^{-7}$ refractive index unit (RIU) (or 0.0944 pg/mm$^2$).

Figure 7:
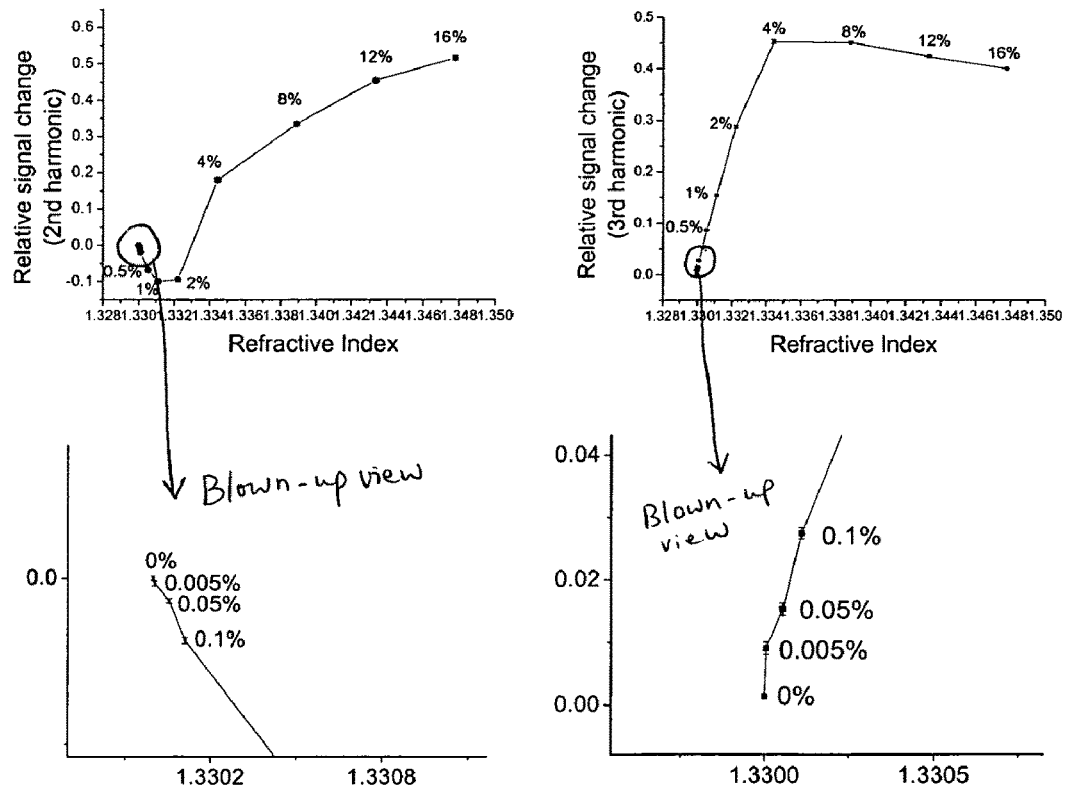
FIG. 7. Graphical representation of relationship of $2^{nd}$ and $3^{rd}$ harmonics as a function of DMSO concentration in water.

FIG. 7 shows the change of the harmonic signal amplitude as a function of DMSO concentration. From the plots, we can see that the relationship between $2^{nd}$ harmonic and the refractive index is quite linear. This is due to the fact that $2^{nd}$ harmonic signal is representing the polarization (reflectivity ratio between p- and s-polarization) of the beam. Furthermore, a "curve-like" relationship is obtained in $3^{rd}$ harmonic since phase information (phase difference between p- and s-polarization) is contributed in $3^{rd}$ harmonic. The phase angle performs a steep change in resonant condition but the change becomes "saturated" if the refractive index variation is too high. Our experimental results demonstrate that the $2^{nd}$ harmonic gives us larger dynamic range of detection. A large dynamic range of measurements can be achieved by using the second harmonic signal for the large RI change regime and the third harmonic signal for the low RI change regime.

A phase-sensitive surface plasmon resonance sensor with simultaneous detection of phase and polarization is demonstrated. An adjustable retarder is employed so that the system can be set in the phase-sensitive region with the compensation of the initial phase shift caused by SPR. Preliminary detection limit of the refractive index for our system is in the order of $10^{-7}$. With temperature stabilization, the sensitivity has room for improvement by suppressing the noise associated with temperature fluctuations. The simultaneous detection of phase and polarization allows us to apply our system in wide range of application with high detection sensitivity as well as large dynamic range.

EXAMPLE 3

This example demonstrates the monitoring of a biomolecular interaction using SPR methodology of the present invention which monitors the phase characteristics of light reflected from the sample. The SPR system setup is the same as that described above.

Materials. Commercially available chemicals were used as received. Phosphate buffered saline (PBS) was obtained from Invitrogen. The Traut's Reagent was obtained from Pierce. Streptavidin-maleimide and its biorecognition partner, alkaline biotinamidocaproyl phosphatase (biotin-protein), bovine serum albumin (BSA) and ethylenediaminetetraacetic acid (EDTA) were obtained from Sigma-Aldrich.

Thiolated BSA preparations. Thiolated BSA was prepared by adding 2 ml of 2% aqueous bovine serum albumin (BSA) to 2 ml of the buffer solution (pH 8, phosphate buffered saline (PBS) with 3 mM EDTA). Next, 400 μl of the Traut's Reagent was added and the solution was stirred slowly for 2 h. This led to the formation of thiolated BSA, which was then purified by dialysis (2 h) against water in a cold room in order to remove excess EDTA. The final product was kept at 4° C. for further use. The streptavidin-BSA complex was prepared by mixing equal molar amounts of streptavidin-maleimide and thiolated BSA. The final concentration of the complex was estimated to be 1.3 μM.

Measurements. In order to demonstrate the real-time biosensing capability of an SPR system of the present invention, a biotin-protein and the streptavidin-BSA complexes were chosen as detection samples. The highly specific interactions between avidin (or streptavidin) and biotin is the basis for these experiments. BSA has been chosen as a model protein whose concentration can be determined by the biosensing method of the present invention. In the first step, biotin-protein was interacted with the gold layer. The protein molecules reacted with the gold layer by non-specific binding and left the biotin groups free for further biorecognition. These free biotin groups were then able to interact with the streptavidin molecules from the streptavidin-BSA complex. This binding was translated into a time-dependent progressive change in the third harmonic signal, with the rate of the signal change depending directly on the concentration of the streptavidin-BSA complex. The specificity of binding was confirmed by the observation of a much weaker change of the third harmonic signal upon injection of equimolar amounts of thiolated BSA without the streptavidin tag.

Figure 8:
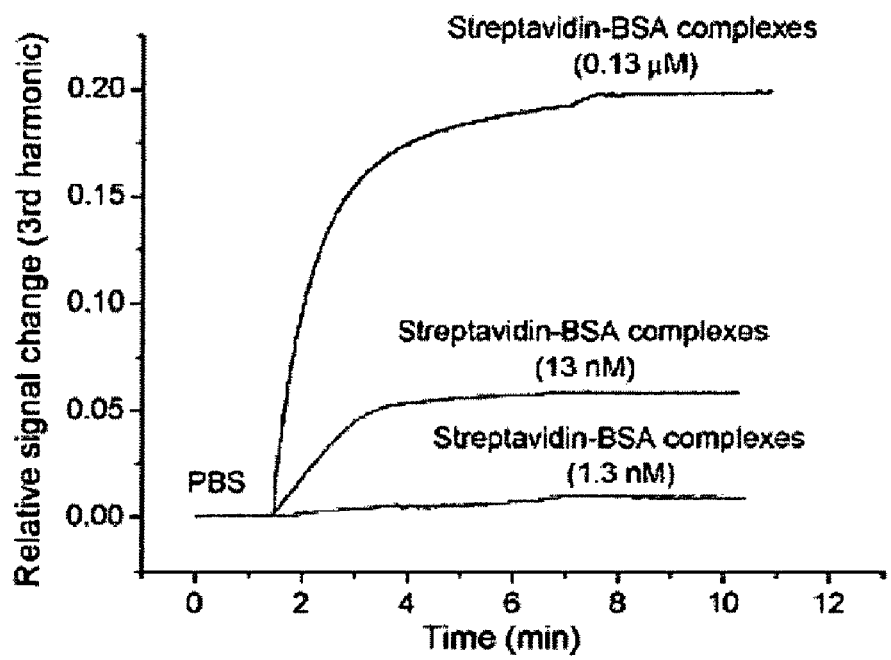
FIG. 8. Graphical representation of response curves obtained by monitoring the third harmonic signal when samples of the streptavidin-BSA complex at various concentrations were injected onto the sensor head.

As the first step, a 40 µg/ml biotin-protein solution was injected into the sensor head containing a pure gold sensor surface (a signal from PBS served as the baseline). The response of the third harmonic is shown in FIG. 8. One can observe that the reaction led to a progressive change of the third harmonic signal until its saturation, suggesting a complete coverage of gold. The exponential character of the response curve confirms that the biotin-protein was indeed immobilized onto the gold surface. One can see that further injection of the PBS buffer did not change the signal, suggesting that the formed complex is strong enough to avoid being washed away. After the monolayer of biotin-protein was immobilized on the gold surface, the signal level due to PBS was taken as the baseline. In the second step, we injected PBS solutions containing different concentrations of streptavidin-BSA complex: 0.13 µM, 13 nM, and 1.3 nM. The effect of such injections on the third harmonic signal is shown in FIG. 8. One can see that the injections were accompanied by sharp changes in the signal, suggesting an efficient binding reaction between biotin and streptavidin. The signal curves follow an exponential shape, typical of a population-related reaction. The data shown in FIG. 8 suggest that our biosensor is capable of detecting streptavidin-BSA complex and biotin-protein binding reaction at a concentration down to 1.3 nM, which exceeds the best reported values. Further sensitivity improvements are possible after applying appropriate surface treatment to the sensing film (e.g. enhance the surface plasmon field strength through the introduction of metallic nanoparticles on the sensor surface) and amplifying the biomolecular signal with surface chemistry (e.g. introduction of functional groups to increase the specificity of the binding reaction).

Figure 9:
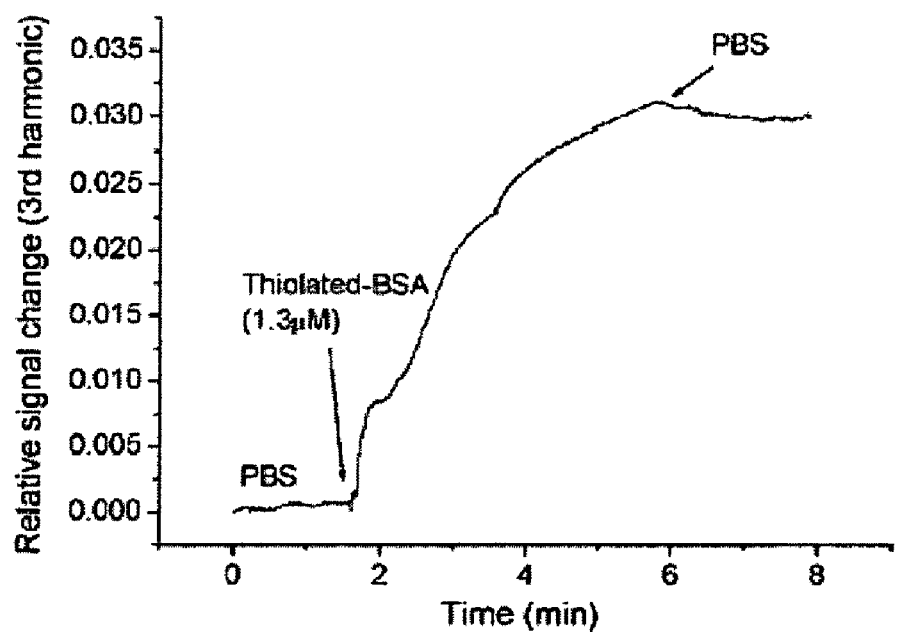
FIG. 9. Graphical representation of response curve obtained from the third harmonic signal when 1.3 μM of thiolated BSA solution was injected onto the metal film immediately after immobilization of biotin-protein on the metal film surface.

Finally, we checked the level of noise due to non-specific binding. For this, we injected a 1.3 µM thiolated BSA sample solution onto the sensor head just after the immobilization of biotin-protein on the sensor surface. FIG. 9 indicates that the signal change due to non-specific binding between BSA and gold surface is about 0.031 units, which is negligible comparing with the specific binding results shown in FIG. 9.

The foregoing demonstrates a novel phase-sensitive surface plasmon resonance biosensor scheme which combines a wide dynamic range with high detection sensitivity. The scheme uses temporal modulation of the excitation beam by a photoelastic modulator and subsequent extraction of phase information at the second and the third harmonics of modulation frequency. The sensitivity of the method for the detection of the streptavidin-BSA complex reached 1.3 nM.

The invention claimed is:

1. A method for detection of an analyte comprising the steps of:
a) providing a transparent substrate having a metal film thereupon, said metal film capable of exhibiting surface plasmon resonance and having analyte binding molecules (ABMs) complexed thereto such that the analyte binding domain of the ABMs is available for analyte binding;
b) contacting the analyte binding domains of a) with a test sample;
c) directing incident light on the surface of the metal film in contact with the substrate to generate reflected light;
d) converting reflected light to an electrical signal, wherein the electrical signal is representative of the polarization and phase of the reflected light; and
e) determining second and third harmonics of the electrical signal,
wherein a difference between the second and/or third harmonics obtained from the test sample and a predetermined control is indicative of the presence or absence of the analyte in the test sample.

2. The method of claim 1 wherein the transparent substrate is a prism.

3. The method of claim 1 wherein the transparent substrate comprises a glass plate and a prism, wherein a refractive index matching oil is disposed between the glass plate and the prism.

4. The method of claim 1 wherein the metal film has a thickness of 45 to 55 nm.

5. The method of claim 1 wherein the metal film consists essentially of gold or silver.

6. The method of claim 1 wherein the incident light is coherent light having a wavelength of 630 nm to 1050 nm.

7. The method of claim 6 wherein the incident light is laser light, wherein the wavelength is selected from the group consisting of 633 nm and 785 nm.

8. The method of claim 1, wherein the predetermined control is generated in the absence of the analyte by passing the reflected light through a phase retarder.

9. The method of claim 1 wherein the second and third harmonics are determined by directing the reflected light through a phase retarder, a photoelastic modulator, a polarizer, and a photodetector, and processing the electrical signal from the photodetector using a lock-in amplifier.

10. The method of claim 1 wherein the incident light is directed at a plurality of spots on the surface of the metal layer in contact with the substrate.

11. A method for detection of an analyte comprising the steps of:
a) providing a transparent substrate having a metal film thereupon, said metal film capable of exhibiting surface plasmon resonance;
b) contacting the surface of the metal film not in contact with the substrate with a test sample;
c) directing incident light on the surface of the metal film in contact with the substrate to generate reflected light;
d) converting reflected light to an electrical signal, wherein the electrical signal is representative of the polarization and phase of the reflected light; and
e) determining second and third harmonics of the electrical signal,
wherein a difference between the second and/or third harmonics obtained from the test sample and a predetermined control is indicative of the presence or absence of the analyte in the test sample.

12. The method of claim 11 wherein the transparent substrate is a prism.

13. The method of claim 11 wherein the transparent substrate comprises a glass plate and a prism, wherein a refractive index matching oil is disposed between the glass plate and the prism.

14. The method of claim 11 wherein the metal film has a thickness of 45 to 55 nm.

15. The method of claim 11 wherein the metal film is consists essentially of gold or silver.

16. The method of claim 11 wherein the incident light is coherent light having a wavelength of 630 nm to 1050 nm.

17. The method of claim 16 wherein the incident light is laser light and wherein the wavelength is selected from the group consisting of 633 nm and 785 nm.

18. The method of claim 11, wherein the wherein the predetermined control is generated in the absence of the analyte by passing the reflected light through a phase retarder.

19. The method of claim 11, wherein the second and third harmonics are determined by directing the reflected light through a phase retarder, a photoelastic modulator, a polarizer, and a photodetector, and processing the electrical signal from the photodetector using a lock-in amplifier.

20. The method of claim 11 wherein the incident light is directed at a plurality of spots on the surface of the metal layer in contact with the substrate.

* * * * *